(12) United States Patent
Bova et al.

(10) Patent No.: US 6,390,982 B1
(45) Date of Patent: May 21, 2002

(54) ULTRASONIC GUIDANCE OF TARGET STRUCTURES FOR MEDICAL PROCEDURES

(76) Inventors: Frank M. Bova, 9429 SW. 1st Pl.;
William A. Friedman, 814 SW. 93rd St., both of Gainesville, FL (US) 32607;
Sanford L. Meeks, 4980 400th St. SE., Iowa City, IA (US) 52245; John M. Buatti, 2891 Saddle Club Rd., Iowa City, IA (US) 52240

( * ) Notice: Subject to any disclaimer, the term of this patent is extended or adjusted under 35 U.S.C. 154(b) by 30 days.

(21) Appl. No.: 09/621,868

(22) Filed: Jul. 21, 2000

Related U.S. Application Data

(60) Provisional application No. 60/145,212, filed on Jul. 23, 1999.

(51) Int. Cl.[7] ............................................... A16B 08/00
(52) U.S. Cl. ..................... 600/443; 600/424; 128/916
(58) Field of Search ............................. 600/443, 442, 600/440, 424, 428; 128/16

(56) References Cited

U.S. PATENT DOCUMENTS

| | | |
|---|---|---|
| 5,027,818 A | 7/1991 | Bova |
| 5,189,687 A | 2/1993 | Bova |
| 5,197,476 A | 3/1993 | Nowacki |
| 5,411,026 A | 5/1995 | Carol |
| 5,447,154 A | 9/1995 | Cinquin |
| 5,588,340 A | 12/1996 | Bova |
| 5,640,960 A | 6/1997 | Jones |
| 5,893,832 A | 4/1999 | Song |
| 5,954,647 A | 9/1999 | Bova |
| 5,999,840 A * | 12/1999 | Grimson et al. ............ 600/424 |
| 6,119,033 A * | 9/2000 | Spigelman et al. ......... 600/426 |
| 6,186,950 B1 * | 2/2001 | Averkiou et al. ........... 600/443 |
| 6,259,943 B1 * | 7/2001 | Cosman et al. ............ 600/429 |

* cited by examiner

Primary Examiner—Francis J. Jaworski
Assistant Examiner—Maulin Patel
(74) Attorney, Agent, or Firm—Miles & Stockbridge; Dennis P. Clarke

(57) ABSTRACT

A system comprising a combination of an ultrasound probe and both passive and active infrared tracking systems. The combined system enables a real time image display of the entire region of interest without probe movement; real time tracking of the target region permitting physiological gating; and probe placement during image acquisition so that all external displacements introduced by the probe can be accounted for at the time of treatment planning. This system may be used in the surgical arena for image guidance during radiation therapy and surgery.

30 Claims, 4 Drawing Sheets

ULTRASONIC GUIDANCE OF TARGET STRUCTURES FOR MEDICAL PROCEDURES

CROSS-REFERENCE TO RELATED APPLICATION

The present application claims the benefit of U.S. Provisional Application No. 60/145,212 filed Jul. 23, 1999.

BACKGROUND OF THE INVENTION

The present invention relates to the imaging of anatomic regions of a patient. More specifically, it relates to a medical system and method using ultrasound in combination with another imaging technology in order to perform a medical procedure upon a patient. The medical procedure can be a diagnostic procedure, a remedial procedure, or a combination of the two.

Among others, Frank J. Bova and William A. Friedman of the present inventors have pioneered the art of high precision planning and treatment of intracranial targets using radiation originating from medical linear accelerators. All of these previously developed planning and treatment systems have been based upon a rigid model consisting of the patient's skull, upper dentisia and intracranial anatomy. Exemplary of these systems and methods are those described in the following U.S. Patent Nos., issued to the Bova and Friedman on the indicated dates, assigned to the assignee of the present application, the entire contents and disclosures of all of which are incorporated herein by reference:

U.S. Pat. No. 5,954,647 Marker system and related stereotactic procedure Sept. 21, 1999

U.S. Pat. No. 5,588,430 Repeat fixation for frameless stereotactic procedure Dec. 31, 1996

U.S. Pat. No. 5,189,687 Apparatus for stereotactic radiosurgery Feb. 23, 1993

U.S. Pat. No. 5,027,818 Dosimetric technique for stereotactic radiosurgery Jul. 02, 1991

Although this rigid model is valid for cranial targets, it is not practical for all anatomic regions. An example of a target that cannot be modeled with a rigid body modality is metastatic disease within the liver. In order to effect the application of high precision radiation treatments or other medical procedures to such deformable anatomic regions, real time imaging of the target region must be incorporated into the treatment procedure.

Among imaging techniques that can be considered for such real time imaging multiplanar x-rays and ultrasound are the best suited.

Multiplanar x-ray imaging, primarily orthogonal imaging, has been used to localize radiation targets for several decades. While this mode of target localization has several advantages, its primary disadvantages are the space and time it requires. The space required by the imaging chain, including x-ray source(s) and imaging electronics, is simply not available near or around a patient who is in position for real time treatment, especially if the treatment uses a medical linear accelerator. Depending on how fast an image of a given portion of the anatomy changes with time and the time required to complete a multiplanar x-ray process, the x-ray imaging may not be sufficiently fast to track changes and provide accurate real time data.

Ultrasonic imaging has the advantage of only requiring a small ultrasonic probe to be utilized near the treatment region. Therefore, it avoids the space problem common to multiplanar x-ray real time imaging during a medical procedure. However, traditional ultrasonic techniques have not generally provided for three-dimensional (3D) anatomical data without requiring movement of the ultrasound probe. Instead, and in the absence of relative movement between the probe and the patient, they have been limited to two-dimensional (2D) imaging.

It has been suggested in the past to use ultrasound for assistance in target localization in several therapeutic settings. Real time imaging of the prostate, for assistance of radioactive seed placement, has been in use for several years. Recently, a 3D real time ultrasound system has been introduced for assistance in such seed placement. This system allows the user to view the prostate in multiple planes while simultaneously introducing catheters for seed placement. Target shifts during surgery have been investigated using a single plane ultrasound probe attached to an image guidance system. The use of a single plane ultrasonic robe attached to an infrared imaging guidance system, in order to obtain surface contours for rigid model registration, has been suggested. The incorporation of a planar ultrasonic probe for anatomic localization of bony anatomy for image guided procedures involving the spine has also been attempted. Real time imaging of the prostate with a planar ultrasound probe attached to an articulating arm to aid in positioning patients for external beam linear accelerator treatments has also been commercially introduced.

The systems that have attempted 3D target localization for external beam targeting have, to date, used single plane ultrasound probes. While this technique allows the user to scan in multiple planes and ultimately reconstruct a 3D image of the target region, the necessary movement of the physical ultrasound probe has presented several significant disadvantages, including (1) the time required to obtain the initial image, (2) the movement of the anatomy as the imaging probe traverses the region, and (3) the inability to view the target region in true three dimensions during treatment when probe movement is impractical. A new ultrasound probe has been introduced which, when linked to a guidance system, can overcome these previous technical limitations.

The new ultrasound or ultrasonic probe was recently introduced by Medison Company. This probe provides a 3D image of an anatomic region without external probe movement. U.S. Pat. No. 5,893,832, issued to Song on Jun. 24, 1997, and assigned on its face to Medison, describes an ultrasound probe, which is able to overcome some of the above-described disadvantages. The probe effectively provides a 3D image of a selected anatomic region without the necessity for external probe movement.

Ultrasound probes like those of the Song patent can provide real time imaging of a portion of the patient's anatomy. However, the image data is with reference to the position of the ultrasound probe. As the ultrasound probe is moved, the point of reference changes. Further, and even if the ultrasound probe is maintained in a relatively stable position, movements of deformable portions of the patient's anatomy such as soft tissue can change the image data. In the case of such changed image data, it may be impossible or quite hard to tell whether the ultrasound probe has moved, the deformable anatomical portion has moved, or both. The ultrasound probe does not provide a fixed frame of reference for properly and readily positioning other medical devices. For example, if one wants to use a medical linear accelerator on the patient, a change in ultrasound image data may indicate that the anatomical portion being targeted has moved such that the patient and/or linear accelerator should be adjusted (usually the patient is moved) accordingly so that the moved target is hit. On the other hand, if the change in ultrasound data simply indicates a movement of the ultrasound probe, the linear accelerator should not be moved. Yet, the ultrasound probe cannot distinguish between those two situations.

Although many of the prior imaging techniques have been generally useful, they have often been subject to one or more of several disadvantages. They may require such bulky equipment that real time imaging is not possible during some medical procedures. Some techniques are unable to track anatomical changes sufficiently fast for certain situations. Some imaging techniques require movement of a device or patient to provide 3D data or they are limited to providing 2D data. Some prior imaging techniques do not provide imaging data relative to a fixed frame of reference such that use of the data in controlling or directing other medical techniques is difficult or impossible.

OBJECTS AND SUMMARY OF THE INVENTION

Accordingly, it is a primary object of the present invention to provide a new and improved imaging method and system.

A more specific object of the present invention is to provide imaging using a combination of imaging techniques.

A further object of the present invention is to provide real time imaging, while allowing ready access to the patient for performing other medical procedures.

Yet another object of the present invention is to provide real time imaging without requiring relative movement between a patient and an imaging device.

Yet another object of the present invention is to provide 3D imaging data.

Yet another object of the present invention is to provide imaging data relatively quickly.

Yet another object of the present invention is to provide imaging data relative to a fixed frame of reference or otherwise especially well-suited to be used in performing medical procedures.

The above and other features of the present invention which will be more readily understood when the following detailed description is considered in conjunction with the accompanying drawings are realized by a method including imaging at least a portion of a patient with a first imaging technique to provide a first set of imaging data, the first set of imaging data having a fixed frame of reference. Further, the method uses imaging at least a part of the patient with a second imaging technique, the part of the patient including at least some of the portion of the patient. The second imaging technique uses an ultrasound device to provide a second set of imaging data, the second set of imaging data being 3D data relative to the ultrasound device and not being fixed relative to the fixed frame of reference. The ultrasound device is operable to provide the 3D data without relative movement between the ultrasound device and the patient. Position data for the ultrasound device is determined. Using the determined position data and the second set of imaging data, a converted set of imaging data corresponding to the second set of imaging data being referenced to the fixed frame of reference is provided. The converted set of image data is combined with at least some of the first set of imaging data to provide a composite set of imaging data.

Preferably, the first imaging technique as used to provide the first set of imaging data is selected from the group consisting of: computerized tomography imaging, magnetic resonance imaging, and fluoroscopic imaging. In one method of the invention, the first imaging technique is performed and completed prior to the imaging with the ultrasound device.

The step of imaging with the ultrasound device uses an ultrasound probe that produces 3D imaging data without relative movement between the ultrasonic probe and the patient. The step of determining position data for the ultrasound probe includes determining the position of a plurality of probe position markers on the ultrasound probe, the position of the probe position markers being determined by a technique not including the first and second imaging techniques. The position of the ultrasound probe is determined using infrared (IR) imaging A medical procedure is performed on the patient using both a medical device and the converted set of imaging data to determine positioning of the medical device relative to the patient. The medical device is a medical linear accelerator. Relative movement is caused between the patient and the medical device to bring the second set of imaging data into registry with the first set of imaging data. The method further includes the step of, at least before completion of the first imaging technique, securing a plurality of patient position markers fixed relative to the patient.

The method of the present invention may alternately be described as including the step of securing a plurality of patient position markers fixed relative to a patient, the patient position markers defining a fixed frame of reference. At least a part of the patient is imaged using an ultrasound device to provide an ultrasound set of imaging data, the ultrasound set of imaging data being 3D data relative to the ultrasound device and not being fixed relative to the fixed frame of reference. The ultrasound device is operable to provide the 3D data without relative movement between the ultrasound device and the patient. Position data for the ultrasound devices determined. The determined position data and the ultrasound set of imaging data are used to provide a converted set of imaging data corresponding to the ultrasound set of imaging data being referenced to the fixed frame of reference.

Preferably, the patient position markers are secured directly to the patient. The step of imaging with the ultrasound device uses an ultrasound probe that produces 3D imaging data without relative movement between the ultrasound probe and the patient. The step of determining position data for the ultrasound probe includes determining the position of a plurality of probe position markers on the ultrasound probe, the position of the probe position markers being determined by a technique not including ultrasound. The position of the ultrasound probe is determined using infrared (IR) imaging.

A medical procedure is performed on the patient using both a medical device and the composite set of imaging data to determine positioning of the medical device relative to the patient. The medical device is a medical linear accelerator.

The method of further includes the steps of: imaging at least a portion of a patient with a non-ultrasound imaging technique to provide a set of imaging data relative to the fixed frame of reference, and combining the converted set of image data with at least some of the set of imaging data from the non-ultrasound imaging technique to provide a composite set of imaging data. The non-ultrasound imaging technique is selected from the group consisting of: computerized tomography imaging, magnetic resonance imaging, and fluoroscopic imaging.

The system of the present invention is described as a system for carrying out medical procedures includes: a plurality of patient position markers operable for fixing relative to a patient to define a fixed frame of reference; an ultrasound device operable to provide an ultrasound set of imaging data, the ultrasound set of imaging data being 3D data relative to the ultrasound device and not being fixed relative to the fixed frame of reference, the ultrasound device being operable to produce 3D data without relative movement between the ultrasound device and the patient; a position determiner to determine position data for the ultrasound device relative to the fixed frame of reference; and a processor operable to use the determined position data and the ultrasound set of imaging data to provide a converted set of imaging data corresponding to the ultrasound set of imaging data being referenced to the fixed frame of reference.

The ultrasound device is an ultrasound probe that produces 3D imaging data without relative movement between the ultrasound probe and the patient. There are a plurality of probe position markers on the ultrasound probe. The position determiner includes a subsystem to determine the position of the probe position markers and the patient position markers. The subsystem includes an infrared (IR) camera.

The system further includes a medical device for performing a medical procedure on a patient using both the medical device and the ultrasound set of imaging data to determine positioning of the medical device relative to the patient.

A non-ultrasonic imaging subsystem is included and is operable to image at least a portion of a patient to provide a set of imaging data relative to the fixed frame of reference. The processor is operable to combine the imaging data from the non-ultrasonic subsystem with the composite data to provide a composite set of imaging data. The non-ultrasonic imaging subsystem is selected from the group consisting of: a computerized tomography system, a magnetic resonance system, and a fluoroscopy system. The medical device a medical linear accelerator.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
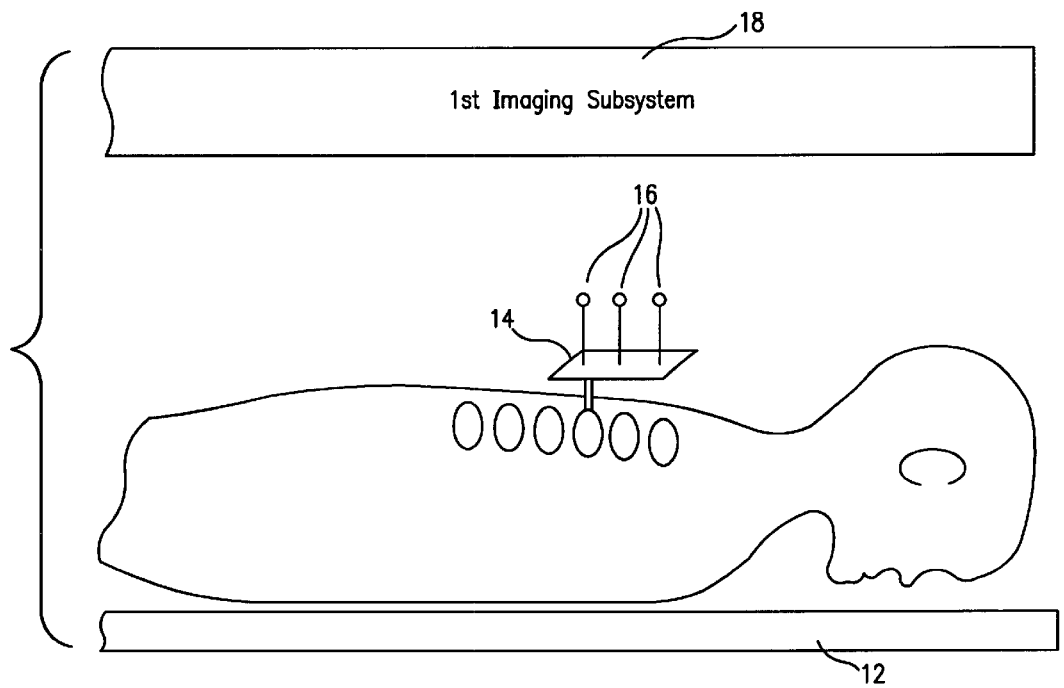
FIG. 1 is a simplified partial side view of a patient illustrating part of the process of the present invention.

Turning now to FIG. 1, a patient is on a table 12 and has a position reference device 14 with a plurality of patient position markers 16 thereon. The reference device 14 is preferably secured directly to a stable (such as skeletal) part of the patient. The markers 16 are preferably passive (reflecting devices) or active devices which can be sensed with an infrared (IR) camera (not shown in FIG. 1, will be shown in FIG. 2, discussed below). The markers and reference device can be constructed with IR reflectors, IR LEDs and various other components as discussed in more detail the various incorporated by reference patents of the present inventors. As illustrated, the device is secured to a bone of the patient.

A first imaging subsystem 18 is used to provide a first set of 3D imaging data corresponding to at least a portion of the patient. The first imaging system 18 is a computerized tomography (CT) system, magnetic resonance (MR), or fluoroscopic system.

Although the first set of imaging data might be collected simultaneously with the ultrasound imaging process that will now be described with reference to FIG. 2, the preferred method involves completing the collection of the first set of imaging data prior to the ultrasound process.

Figure 2:
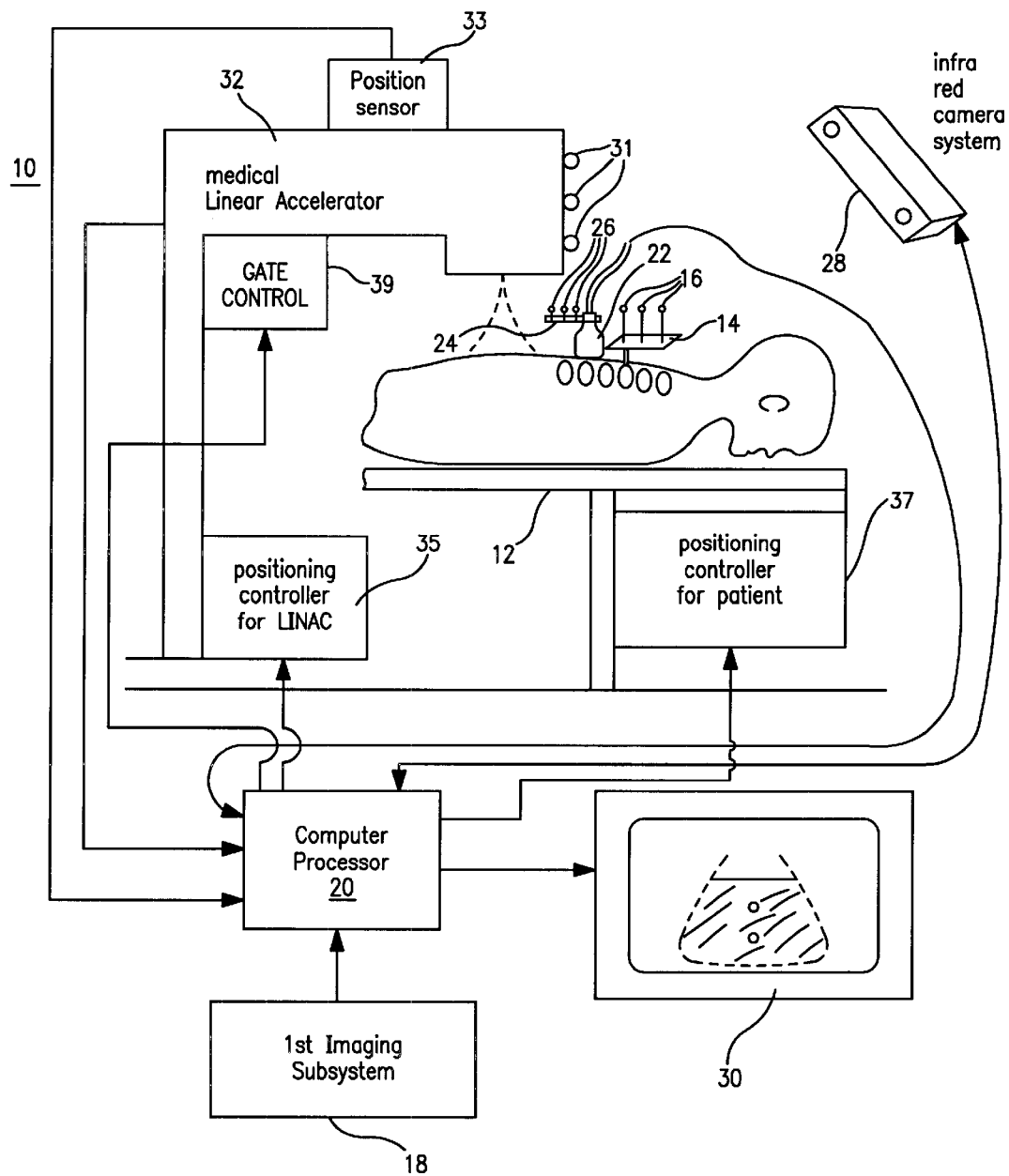
FIG. 2 is a simplified partial side view of a patient with block diagrams of components of a system according to the present invention.

Turning to FIG. 2, the system 10 according to the present invention includes the table 12, reference device 14, markers 16, and imaging subsystem 18 as discussed above. Additionally, a processor 20 receives the first set of imaging data from the imaging subsystem 18.

An ultrasound device such as 3D ultrasound probe 22 of the type in the Song patent is part of a second imaging subsystem. The probe 22 provides 3D imaging data to the processor 20. A reference device 24 is fixed to the probe 22 and has probe position markers 26. The reference device 24 is similar in construction to device 14 and has markers similar to markers 16. Reference device 24 differs from device 14 in that device 24 may have fasteners (not shown) or otherwise be fixed to the probe 22.

The markers 16 and 26 are tracked using an infrared (IR) camera system 28 and techniques described in the present inventors' prior incorporated by reference patents. IR system 28 is connected to processor 20, which can then convert the ultrasound data into data relative to the frame of reference of the device 14. The device 14 is, at that stage, stationary relative to the fixed frame of reference of the IR system 28 (more generally, the fixed frame of reference is the room in which the patient is then located). Thus, the ultrasound data is converted to be defined relative to this fixed frame of reference.

If the internal organ or other soft tissue to be treated has moved relative to the spine to which reference 14 is attached, a comparison of ultrasound image and the CT or other set of first imaging data will show an offset. For example, if there are three tumors in the patient's liver, an offset between their positions in the ultrasound image and the first imaging data indicates movement. By bringing the tumors or other prominent features in the ultrasound display into registry with their positions in the first data set, one can tell how much position adjustment is required. For example, and given a set of orthogonal x, y, z axes, suppose a comparison of the ultrasound image with the first imaging data shows that the internal organ of interest is offset 1 mm in the x dimension, 1.5 mm in the y dimension, and 2 mm in the z dimension. One can then move the patient relative to the accelerator 1 mm in the x dimension, 1.5 mm in the y dimension, and 2 mm in the z dimension in the appropriate directions such that the ultrasound image now registers with the first imaging data. There are several ways that this could be done.

The display 30 shows images combining the ultrasound data from probe 22 and imaging data from imaging subsystem 18. This may show the offset and the medical staff may manually adjust the patient in z, y, z dimensions until the offset is effectively zero. Alternately, the imaging processing software within the computer processor 20 may automatically bring the ultrasound images into registry with the first imaging data and then direct the medical staff that the patient should be moved accordingly. A further alternative would use LEDs 31 (or other markers) on linear accelerator 32 and/or position sensor 33 to sense its position and one or more of linear accelerator positioning controller 35 and patient positioning controller 37. In that case, components 31, 33, 35, and 37 would be constructed and work in the fashion of components 166, 164, 170, and 172 of the incorporated by reference U.S. Pat. No. 5,954,647 patent. Further, a feedback arrangement (not specifically shown) like those of the '647 patent could be used to automatically bring the patient (or portion of the patient) into proper relative position and orientation.

A medical device such as a medical linear accelerator 32 can then use the imaging data including the ultrasound imaging data combined into the first set of imaging data with the ultrasound data having been converted to be relative to the fixed frame of reference. Therefore, the medical device 32 can use the ultrasound data for targeting the radiation to the proper part of the patient. By combining the ultrasound data with the first imaging data (CT, MRI, or fluoroscopic) one gets the real time ultrasound data combined with the higher resolution first imaging data, An additional advantage of combining the ultrasound with the higher resolution first imaging data is that physiological gating could be used. Suppose one is treating a patient's colon and the colon is oscillating. A gate control 39 is activated to allow radiation to only get to the patient when the processor 20 senses from the ultrasound data from probe 22 that the colon is in the proper position. The accelerator is pulsed on only when the position is proper.

Figure 3:
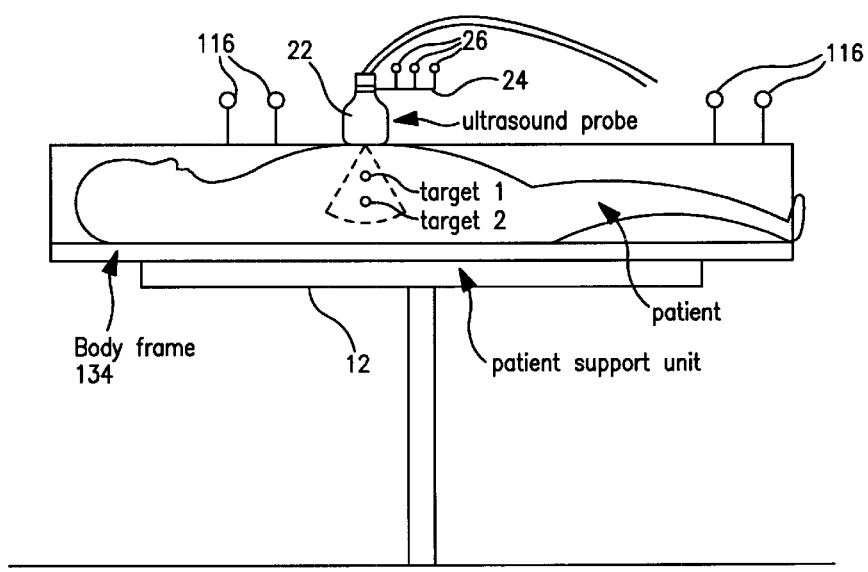
FIG. 3 is a simplified partial side view of a patient with various alternate components.

As described with respect to FIGS. 1 and 2, the technique uses a reference device 14 connected directly to the patient and uses the linear accelerator 32 as the medical device. With reference now to FIG. 3, alternate arrangements to those components are shown. It should be understood that the imaging subsystem 18, processor 20, IR camera system 28, and display 30 are not shown in FIG. 3 for ease of illustration, but such components would be used in the FIG. 3 system. Likewise, components such as 31, 33, 35, and 37 are not shown in FIG. 3, but may be used in conjunction with this arrangement.

The FIG. 3 arrangement uses components 12, 22, 24, and 26 as described with respect to FIGS. 1 and 2. Additionally, and in lieu of the reference device 14 attached directly to the patient, markers 116 are attached to a body frame 134. As the patient is secured to the body frame 134, the markers 116 are constructed and operable in the same fashion as the markers 16. For ease of illustration, FIG. 3 does not show the linear accelerator or other medical device that would be positioned relative to the patient using the imaging system. By using the imaging data from the ultrasound probe after it has been referenced to the fixed frame of reference (markers 116), the relative positioning of the patient and the medical device can be precisely controlled. It should be understood that the body frame 134 with fidicial markers 116 thereon could also be used with the linear accelerator 32 of FIG. 2.

Figure 4:
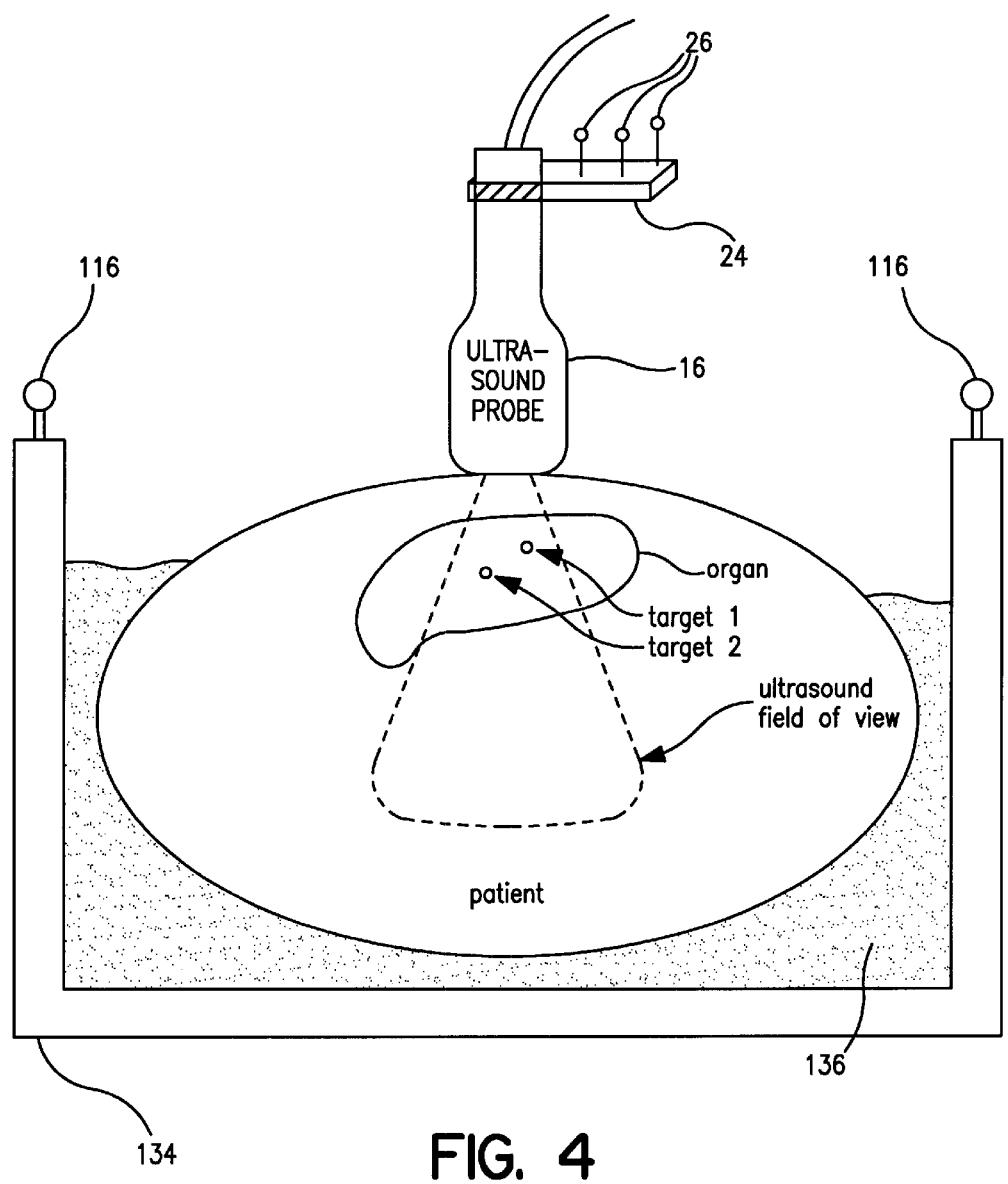
FIG. 4 is a simplified end view of a patient with internal sections shown in conjunction portions of the components of FIG. 3.
Figure 5:
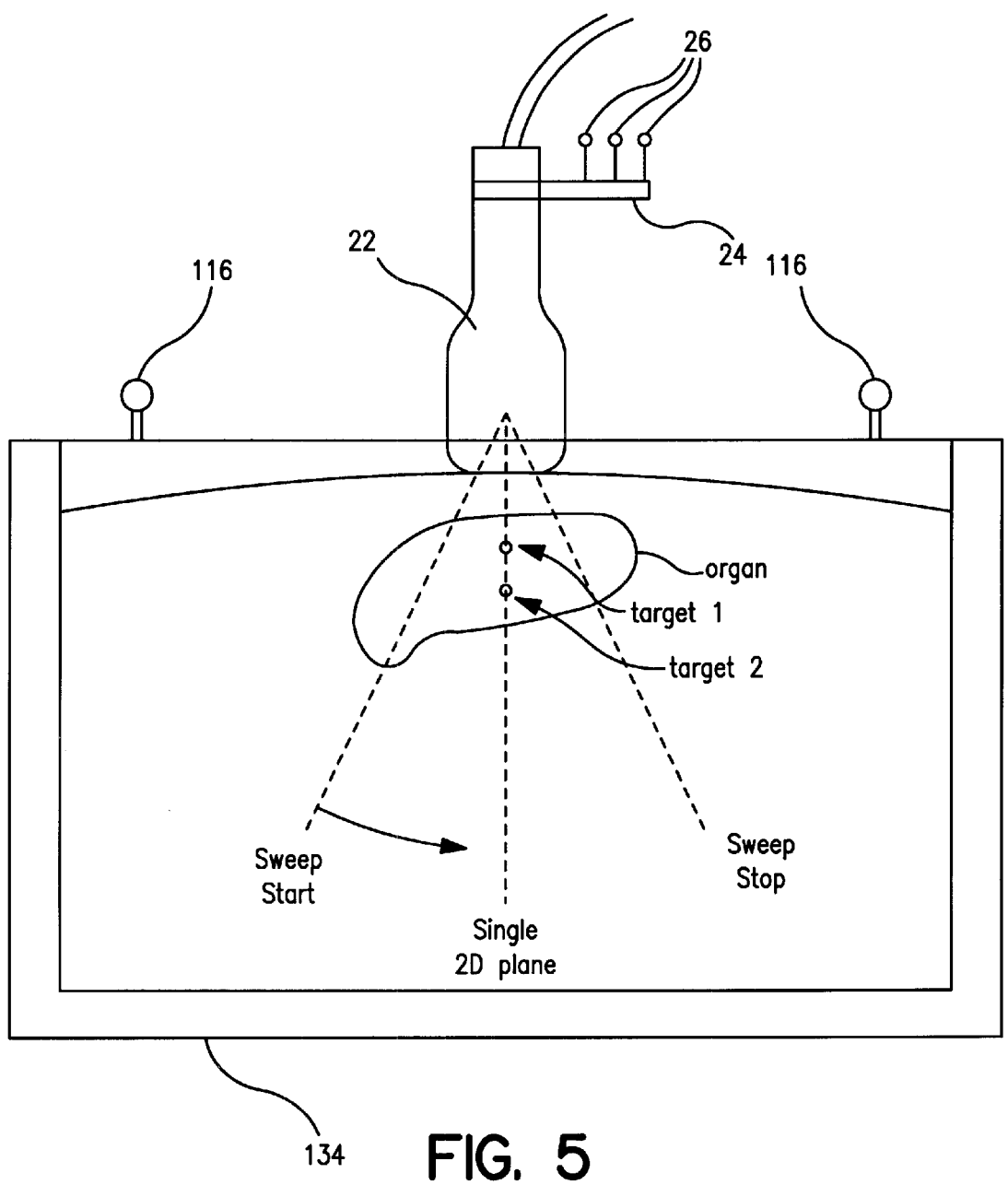
FIG. 5 is a simplified end view of a patient with internal sections shown in conjunction portions of the components of FIG. 4.

FIGS. 4 and 5 respectively show end and side views with parts broken away of the patient and showing padding 136 to hold the patient in position.

The operation of the method of the present invention will now be discussed. The ultrasound probe is tracked using either passive or active infrared guidance or any other tracking system including mechanical (i.e. articulating arms), magnetic, ultrasound, radio frequency (rf), etc. for the probe relative to the fixed reference system. The ultrasound probe may be a device that is approximately 1.5 inches by 3 inches by 6 inches high. The device is held with the 1.5-inch by 3-inch section against the patient. Other size probes, including smaller probes, could alternately be used. The probe can scan in one of two modes. In the first mode, the probe acquires a single ultrasound plane. This plane is pie-shaped and the depth of the ultrasound unit can control the angle. In the second mode, the probe can sweep this single plane perpendicular to the single plane mode, thus obtaining a series of 2D slices creating a 3D view of the anatomy. Either the 2D or 3D scan parameters can be set so that the data obtained from repeat scans is in the exact same spatial relationship to the surface of the probe.

Through a calibration procedure, the various picture elements (pixels) of the ultrasound image can be related to a fixed reference attached to the probe. The reference system that is used can track a set of geometric markers in one of two modes. The first mode is to have the reference markers be light-emitting infrared diodes known as IR LEDs. The position of each IR LED can be precisely determined by the use of the set of infrared cameras 28. The second method is to make each reference marker a reflective sphere and use an infrared camera system that can track reflective or passive markers. In either case, the attachment of a reference array 24 of markers to the ultrasound probe allows the calibration of the ultrasound image space to a known reference. In the radiation therapy vault, this space may be the isocenter of the teletherapy unit. In the operating room, this space may be a secondary reference attached to either the patient or some surgical instrument.

The 3D probe can be calibrated for correlation to image space in either 2D or 3D mode. The above calibration procedure requires that an object with known ultrasound targets be positioned relative to a known reference system. In the case of a radiation therapy teletherapy unit, this is usually the center of rotation of the teletherapy unit, know as the isocenter. For the operative suite, this may be a reference arc system that is attached to the patient in a fixed rigid geometry. The initial ultrasound image is obtained and the ultrasound target on the 2D or 3D image is identified and correlated to the known target points. A calibration matrix that can then map all subsequent ultrasound images to this known reference space is then possible.

The 3D guidance allows for identification of the target region. The 2D guidance allows for more rapid image correlation and physiological gating to track patient movement due to breathing or blood flow.

The acquisition of a 3D-ultrasound image takes longer than a 2D image. When organ motion due to breathing, blood flow or patient movement must be tracked, there is an advantage of tracking with the more rapidly obtained and, therefore, more rapidly repeated 2D scanning technique. For the identification of the anatomic targets, it is important to have the full 3D data set. It is, therefore, expedient to be able to move between 2D and 3D scanning. This is especially advantageous if the ultrasound probe can be switched back and forth between the two modes without probe movement.

If combined with a second rigid reference system (either passive or active) attached to the patient such as a biteplate or reference array anchored to a bony landmark, the stereotactic probe image can be automatically fused and displayed with other 3D images such as CT, MR or any other imaging that provides a 3D data set. If the reference system discussed above is of the type which is rigidly fixed to the patient's anatomy, and if the patient undergoes a medical exam which allows the patient's anatomy to be known relative to this reference, then the data from the ultrasound probe can be displayed so that it automatically correlates with the initial imaging data base. For example, assume that the patient has a reference system attached to their head that is made of infrared reflective spheres. Once the scan has been taken, these spheres can be identified in the 3D database and the position of all of the anatomy within the data set would be known relative to these markers. Further assume that the ultrasound probe is calibrated so that the ultrasound image can be correlated to the same object space as the CT image. As the probe images the patient's head, the CT plane, which matches the ultrasound plane, can be displayed.

Although specific constructions have been presented, it is to be understood that these are for illustrative purposes only. Various modifications and adaptations will be apparent to those of skill in the art. Therefore, the scope of the present invention should be determined by reference to the claims.

What is claimed is:

1. A method comprising the steps of:
   imaging at least a portion of a patient with a first imaging technique to provide a first set of imaging data, the first set of imaging data having a fixed frame of reference;
   imaging at least a part of the patient with a second imaging technique, the part of the patient including at least some of the portion of the patient, the second imaging technique using an ultrasound device to provide a second set of imaging data, the second set of imaging data being 3D data relative to the ultrasound device and not being fixed relative to the fixed frame of reference, the ultrasound device being operable to provide the 3D data without relative movement between the ultrasound device and the patient;
   determining position data for the ultrasound device;
   using the determined position data and the second set of imaging data to provide a converted set of imaging data corresponding to the second set of imaging data being referenced to the fixed frame of reference; and
   combining the converted set of image data with at least some of the first set of imaging data to provide a composite set of imaging data.

2. The method of claim 1 wherein the first imaging technique as used to provide the first set of imaging data is selected from the group consisting of:
   computerized tomography imaging, magnetic resonance imaging, and fluoroscopic imaging.

3. The method of claim 2 wherein the first imaging technique is performed and completed prior to the imaging with the ultrasound device.

4. The method of claim 2 wherein the step of imaging with the ultrasound device uses an ultrasound probe that produces 3D imaging data without relative movement between the ultrasonic probe and the patient.

5. The method of claim 4 wherein the step of determining position data for the ultrasound probe includes determining the position of a plurality of probe position markers on the ultrasound probe, the position of the probe position markers being determined by a technique not including the first and second imaging techniques.

6. The method of claim 5 wherein the position of the ultrasound probe is determined using infrared (IR) imaging.

7. The method of claim 5 further comprising the step of performing a medical procedure on the patient using both a medical device and the converted set of imaging data to determine positioning of the medical device relative to the patient.

8. The method of claim 7 wherein the medical device is a medical linear accelerator.

9. The method of claim 1 further comprising the steps of:
   performing a medical procedure on the patient using both a medical device and the converted set of imaging data to determine positioning of the medical device relative to the patient;
   and causing relative movement between the patient and the medical device to bring the second set of imaging data into registry with the first set of imaging data.

10. The method of claim 1 further comprising the step of, at least before completion of the first imaging technique, securing a plurality of patient position markers fixed relative to the patient.

11. A method comprising the steps of:
   securing a plurality of patient position markers fixed relative to a patient, the patient position markers defining a fixed frame of reference;
   imaging at least a part of the patient using an ultrasound device to provide an ultrasound set of imaging data, the ultrasound set of imaging data being 3D data relative to the ultrasound device and not being fixed relative to the fixed frame of reference, the ultrasound device being operable to provide the 3D data without relative movement between the ultrasound device and the patient;
   determining position data for the ultrasound device;
   using the determined position data and the ultrasound set of imaging data to provide a converted set of imaging data corresponding to the ultrasound set of imaging data being referenced to the fixed frame of reference.

12. The method of claim 11 wherein the patient position markers are secured directly to the patient.

13. The method of claim 11 wherein the step of imaging with the ultrasound device uses an ultrasound probe that produces 3D imaging data without relative movement between the ultrasound probe and the patient.

14. The method of claim 13 wherein the step of determining position data for the ultrasound probe includes determining the position of a plurality of probe position markers on the ultrasound probe, the position of the probe position markers being determined by a technique not including ultrasound.

15. The method of claim 14 wherein the position of the ultrasound probe is determined using infrared (IR) imaging.

16. The method of claim 15 further comprising the step of performing a medical procedure on the patient using both a medical device and the composite set of imaging data to determine positioning of the medical device relative to the patient.

17. The method of claim 16 wherein the medical device is a medical linear accelerator.

18. The method of claim 15 further comprising the steps of:
   imaging at least a portion of a patient with a non-ultrasound imaging technique to provide a set of imaging data relative to the fixed frame of reference, and combining the converted set of image data with at least some of the set of imaging data from the non-ultrasound imaging technique to provide a composite set of imaging data.

19. The method of claim 18 wherein the non-ultrasound imaging technique is selected from the group consisting of:
   computerized tomography imaging, magnetic resonance imaging, and fluoroscopic imaging.

20. A system for carrying out medical procedures comprising:
- a plurality of patient position markers operable for fixing relative to a patient to define a fixed frame of reference;
- an ultrasound device operable to provide an ultrasound set of imaging data, the ultrasound set of imaging data being 3D data relative to the ultrasound device and not being fixed relative to the fixed frame of reference, the ultrasound device being operable to produce 3D data without relative movement between the ultrasound device and the patient;
- a position determiner to determine position data for the ultrasound device relative to the fixed frame of reference; and
- a processor operable to use the determined position data and the ultrasound set of imaging data to provide a converted set of imaging data corresponding to the ultrasound set of imaging data being referenced to the fixed frame of reference.

21. The system of claim 20 wherein the ultrasound device is an ultrasound probe that produces 3D imaging data without relative movement between the ultrasound probe and the patient.

22. The system of claim 21 further comprising a plurality of probe position markers on the ultrasound probe.

23. The system of claim 22 wherein the position determiner includes a subsystem to determine the position of the probe position markers and the patient position markers.

24. The system of claim 23 wherein the subsystem includes an infrared (IR) camera.

25. The system of claim 22 further comprising a medical device for performing a medical procedure on a patient using both the medical device and the ultrasound set of imaging data to determine positioning of the medical device relative to the patient.

26. The system of claim 20 further comprising a medical device for performing a medical procedure on a patient using both the medical device and the ultrasound set of imaging data to determine positioning of the medical device relative to the patient.

27. The system of claim 20 further comprising a non-ultrasonic imaging subsystem operable to image at least a portion of a patient to provide a set of imaging data relative to the fixed frame of reference and wherein the processor is operable to combine the imaging data from the non-ultrasonic subsystem with the composite data to provide a composite set of imaging data.

28. The system of claim 27 wherein the non-ultrasonic imaging subsystem is selected from the group consisting of:
- a computerized tomography system, a magnetic resonance system, and a fluoroscopy system.

29. The system of claim 28 further comprising a medical device for performing a medical procedure on a patient using both the medical device and the ultrasound set of imaging data to determine positioning of the medical device relative to the patient.

30. The system of claim 29 wherein the medical device a medical linear accelerator.

* * * * *

UNITED STATES PATENT AND TRADEMARK OFFICE
CERTIFICATE OF CORRECTION

PATENT NO. : 6,390,982 B1
DATED : May 21, 2002
INVENTOR(S) : Frank J. Bova

It is certified that error appears in the above-identified patent and that said Letters Patent is hereby corrected as shown below:

<u>Title page,</u>
Item [75], Inventor, please enter -- Assignee: University of Florida, Gainesville, FL (US) --.

Signed and Sealed this

Nineteenth Day of November, 2002

Attest:

JAMES E. ROGAN
Attesting Officer                Director of the United States Patent and Trademark Office

UNITED STATES PATENT AND TRADEMARK OFFICE
CERTIFICATE OF CORRECTION

PATENT NO. : 6,390,982 B1
DATED : May 21, 2002
INVENTOR(S) : Frank J. Bova

It is certified that error appears in the above-identified patent and that said Letters Patent is hereby corrected as shown below:

<u>Title page,</u>
Item [76], please change the spelling of the inventor's name from "Frank M. Bova" to -- Frank J. Bova --.

Signed and Sealed this

Seventeenth Day of December, 2002

JAMES E. ROGAN
*Director of the United States Patent and Trademark Office*